US009603732B2

(12) United States Patent
Ma et al.

(10) Patent No.: US 9,603,732 B2
(45) Date of Patent: Mar. 28, 2017

(54) STENT INCLUDING SINUSOIDAL STRUTS

(71) Applicant: Covidien LP, Mansfield, MA (US)

(72) Inventors: Jianlu Ma, Irvine, CA (US); Ott Khouengboua, Chaska, MN (US); Alex Grafov, Eden Prairie, MN (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/628,380

(22) Filed: Feb. 23, 2015

(65) Prior Publication Data

US 2015/0230952 A1    Aug. 20, 2015

Related U.S. Application Data

(63) Continuation of application No. 11/912,616, filed as application No. PCT/US2006/015596 on Apr. 25, 2006, now Pat. No. 8,961,585.

(60) Provisional application No. 60/674,859, filed on Apr. 25, 2005.

(51) Int. Cl.
    *A61F 2/06*     (2013.01)
    *A61F 2/89*     (2013.01)
    *A61F 2/915*     (2013.01)

(52) U.S. Cl.
    CPC ........ *A61F 2/89* (2013.01); *A61F 2002/9155* (2013.01)

(58) Field of Classification Search
    CPC .. A61F 2/856; A61F 2/89; A61F 2/915; A61F 2002/91525; A61F 2002/91558
    See application file for complete search history.

(56) References Cited

U.S. PATENT DOCUMENTS

| | | | |
|---|---|---|---|
| 4,503,569 | A | 3/1985 | Dotter |
| 4,580,568 | A | 4/1986 | Gianturco |
| 4,739,762 | A | 4/1988 | Palmaz |
| 5,026,377 | A | 6/1991 | Burton et al. |
| 5,059,211 | A | 10/1991 | Stack et al. |
| 5,192,297 | A | 3/1993 | Hull |
| 5,222,971 | A | 6/1993 | Willard et al. |
| 5,421,955 | A | 6/1995 | Lau et al. |
| 5,449,373 | A | 9/1995 | Pinchasik et al. |
| 5,476,508 | A | 12/1995 | Amstrup |

(Continued)

FOREIGN PATENT DOCUMENTS

| | | |
|---|---|---|
| DE | 19749691 A1 | 4/1999 |
| DE | 20308672 U1 | 10/2003 |

(Continued)

OTHER PUBLICATIONS

Dictionary.com definition for "unconnected" as accessed Jun. 28, 2016; http://www.dictionary.com/browse/unconnected.*

(Continued)

*Primary Examiner* — Jonathan Miles

(57) ABSTRACT

The invention provides for intra-luminal stents, especially stent having controlled fracture connection, as well as, methods of making and using the same. In one embodiment, a stent for implantation into a vessel has a plurality of annular segments collectively forming tubular shape, characterized by at least first and second adjacent annular segments each defined by a plurality of struts and at least one joint interconnecting respective struts of the first and second segments on a non-permanent basis.

23 Claims, 3 Drawing Sheets

(56) References Cited

U.S. PATENT DOCUMENTS

| | | |
|---|---|---|
| 5,514,154 A | 5/1996 | Lau et al. |
| 5,603,721 A | 2/1997 | Lau et al. |
| 5,632,762 A | 5/1997 | Myler |
| 5,702,418 A | 12/1997 | Ravenscroft |
| 5,728,158 A | 3/1998 | Lau et al. |
| 5,735,893 A | 4/1998 | Lau et al. |
| 5,749,890 A | 5/1998 | Shaknovich |
| 5,817,152 A | 10/1998 | Birdsall et al. |
| 6,001,124 A | 12/1999 | Bachinski |
| 6,056,776 A | 5/2000 | Lau et al. |
| 6,066,167 A | 5/2000 | Lau et al. |
| 6,120,522 A | 9/2000 | Vrba et al. |
| 6,126,645 A | 10/2000 | Thompson |
| 6,146,403 A | 11/2000 | St. Germain |
| 6,231,598 B1 | 5/2001 | Berry et al. |
| 6,258,117 B1 | 7/2001 | Camrud et al. |
| 6,264,688 B1 | 7/2001 | Herklotz et al. |
| 6,350,277 B1 | 2/2002 | Kocur |
| D458,679 S | 6/2002 | Thompson et al. |
| 6,432,133 B1 | 8/2002 | Lau et al. |
| 6,485,510 B1 | 11/2002 | Camrud et al. |
| 6,485,511 B2 | 11/2002 | Lau et al. |
| 6,585,753 B2 | 7/2003 | Eder et al. |
| 6,596,022 B2 | 7/2003 | Lau et al. |
| 6,607,551 B1 | 8/2003 | Sullivan et al. |
| 6,613,077 B2 | 9/2003 | Gilligan et al. |
| 6,699,280 B2 | 3/2004 | Camrud et al. |
| 6,746,475 B1 | 6/2004 | Rivelli, Jr. |
| 6,752,829 B2 | 6/2004 | Kocur et al. |
| 6,796,999 B2 | 9/2004 | Pinchasik |
| 6,878,160 B2 | 4/2005 | Gilligan et al. |
| 6,899,730 B1 | 5/2005 | Rivelli, Jr. |
| 7,033,385 B2 | 4/2006 | Eder et al. |
| 7,037,327 B2 | 5/2006 | Salmon et al. |
| 7,105,015 B2 | 9/2006 | Goshgarian |
| 7,172,617 B2 | 2/2007 | Colgan et al. |
| 7,175,654 B2 | 2/2007 | Bonsignore et al. |
| 7,214,240 B2 | 5/2007 | Bonsignore et al. |
| 8,961,585 B2 | 2/2015 | Ma et al. |
| 2001/0039447 A1* | 11/2001 | Pinchasik ............ A61F 2/91 623/1.15 |
| 2003/0033001 A1 | 2/2003 | Igaki |
| 2003/0045926 A1 | 3/2003 | Pinchasik |
| 2003/0114918 A1* | 6/2003 | Garrison ............ A61F 2/07 623/1.13 |
| 2003/0135266 A1 | 7/2003 | Chew et al. |
| 2004/0106977 A1 | 6/2004 | Sullivan et al. |
| 2004/0236406 A1 | 11/2004 | Gregorich |
| 2005/0033399 A1 | 2/2005 | Richter |
| 2005/0055080 A1 | 3/2005 | Istephanous et al. |
| 2006/0206187 A1 | 9/2006 | Parker et al. |
| 2006/0247759 A1 | 11/2006 | Burpee et al. |

FOREIGN PATENT DOCUMENTS

| | | |
|---|---|---|
| EP | 0699087 A1 | 3/1996 |
| EP | 1173109 A1 | 1/2002 |
| EP | 1223891 A1 | 7/2002 |
| EP | 1290987 A2 | 12/2003 |
| EP | 1372530 A2 | 1/2004 |
| EP | 1005843 A2 | 1/2005 |
| WO | WO 9427667 A1 | 12/1994 |
| WO | WO 9531945 A1 | 11/1995 |
| WO | WO 9830172 A1 | 7/1998 |
| WO | WO 9912495 A1 | 3/1999 |
| WO | WO 9965418 A1 | 12/1999 |
| WO | WO 0015151 A1 | 3/2000 |
| WO | WO 0032136 A1 | 6/2000 |
| WO | WO 0041649 A1 | 7/2000 |
| WO | WO 0062708 A1 | 10/2000 |
| WO | WO 0066031 A1 | 11/2000 |
| WO | WO 0101888 A1 | 1/2001 |
| WO | WO 0132102 A1 | 5/2001 |
| WO | WO 02076340 A2 | 10/2002 |
| WO | WO 03075797 A2 | 9/2003 |
| WO | WO 2005118971 A2 | 12/2005 |
| WO | 2006087621 A1 | 8/2006 |
| WO | WO 2006116383 A2 | 11/2006 |

OTHER PUBLICATIONS

Extended European Search Report from counterpart European Application No. EP 13157110.1, dated Jun. 13, 2014, 8 pages.
Prosecution History from U.S. Appl. No. 11/912,616, dated Oct. 25, 2007 through Oct. 15, 2014, 192 pp.
Examination Report from counterpart European Application No. 06751348.1, dated May 30, 2016, 3 pp.

* cited by examiner

STENT INCLUDING SINUSOIDAL STRUTS

This application is a continuation of U.S. patent application Ser. No. 11/912,616 by Ma et al., filed on Apr. 25, 2006, which is a national stage application entry under 35 U.S.C. §371 of PCT Application Ser. No. PCT/US2006/015596, filed Apr. 25, 2006, which claims the benefit of U.S. Provisional Patent Application Ser. No. 60/674,859, filed Apr. 25, 2005, the disclosures of each of which are incorporated herein by reference in their entirety.

FIELD OF THE INVENTION

The invention relates generally to the field of prosthetic medical devices, and, more particularly to designs for intraluminal stents.

BACKGROUND OF THE INVENTION

Stents are prosthetic devices implanted within a subject's vessel lumen to maintain the patency of the vessel. Typically stents are comprised of cylindrical members, which are capable of expanding from a smaller diameter to a larger diameter. The stent is typically implanted within a patient's vasculature by a minimally invasive procedure using a catheter and guide wire. The catheter serves as a delivery device to transport the stent to its implantation site, e.g. an occluded vessel lumen. Once delivered to the desired site, the stent is expanded from its smaller delivery diameter to its larger diameter. A balloon-expandable stent is caused to expand by inflating the underlying balloon located at the distal end of the catheter, and a self-expanding stent is allowed to expand by releasing it from a sheath located at the distal end of the catheter. Ultimately, the stent is deployed against the interior lining of subject's vessel wall. The expansion force of the expanded stent expansion opens up the vessel occlusion. The structural integrity of the stent operates as scaffolding to support the vessel lumen and maintain its patency.

A variety of vascular stents are known, such as U.S. Pat. No. 3,657,744 (Ersek), U.S. Pat. No. 3,868,956 (Alfidi), U.S. Pat. No. 4,441,216 (Ionescu), U.S. Pat. No. 4,503,569 (Dotter), U.S. Pat. No. 4,512,338 (Blako), U.S. Pat. No. 4,553,545 (Maass), U.S. Pat. No. 4,580,568 (Gianturco), U.S. Pat. No. 4,733,665 (Palmaz), U.S. Pat. No. 4,762,128 (Rosenbluth), U.S. Pat. No. 4,800,882 (Gianturco), U.S. Pat. No. 4,856,516 (Hillstead), U.S. Pat. No. 4,886,062 (Wiktor), U.S. Pat. No. 5,421,955 (Lau), U.S. Pat. No. 5,476,508 (Amstrup), U.S. Pat. No. 5,514,154 (Lau), U.S. Pat. No. 5,449,373 (Pinchasik), U.S. Pat. No. 5,695,516 (Fischell), U.S. Pat. No. 6,231,598 (Berry).

Because stents are usually deployed through a subject's vasculature, which can often involve navigating through both narrow and curved vessels, it is advantageous for the stent to be flexible along its longitudinal axis. Loading conditions generate significant amounts of stress on the stent involving torsion, extension, compression and flexion. Once deployed, the stent must have sufficient radial strength to resist compressive forces in order to maintain vessel patency. In addition, where the stent is deployed in a vessel, which undergoes regular stress such as by bending or where the vessel itself is curved, flexibility and resistance to fracture of the deployed stent may also be important.

A need exists for an improved stent design that will provide sufficient radial strength to maintain vessel patency while at the same time provides sufficient flexibility to facilitate easy deployment and accommodation of the particular physiological stress factors associated with the vessel in which it is deployed while also resisting fatigue fracture as a result of those same stress factors. Further, a need exists for a modular stent that is capable of separating at predetermined points in response to stress, in lieu of fracturing haphazardly. Embodiments of the invention described below meets these needs as well.

SUMMARY OF THE INVENTION

In certain embodiments the invention provides a stent which may be implanted in the vessel lumen of a subject in order to maintain or improve the patency of the vessel. Some embodiments of the invention provide a stent with improved resistance to fracture in certain implantation sites, as well as improved flexibility suitable for traversing through and deployment in tortuous vasculature. For example, certain stents of the invention may be used in the superficial femoral or iliac arteries. The stent may be expandable and thus have a first (smaller) and second (larger) diameter. The first diameter may be suitable for delivery of the stent to its implant site, while the second diameter, i.e., the deployed expanded diameter, is approximately the diameter of the vessel lumen at the implant site and is thus suitable for maintaining the vessel patency. According to a first aspect of the invention, a stent for implantation into a vessel comprising a plurality of annular segment's collectively forming tubular shape, characterized by at least first and second adjacent annular segments each defined by a plurality of struts; and at least one joint interconnecting respective struts of the first and second segments on a non-permanent basis. In one embodiment, the interconnecting joint comprises a first male interlocking structure and a second female interlocking structure. In another embodiment, the respective struts of the first and second segments each comprise a hole and the interconnecting joint projects through the hole in the respective struts of the first and second segments. In still other embodiment, the interconnecting joint has a first end and a second end, and the first and second ends are each thicker than the diameter of one of the holes in the respective struts of the first and second segments. In other embodiments the interconnecting joint separates after the stent is deployed or at least a portion of the stent may comprise shape memory material such as nitinol or a shape memory polymer.

The invention also provides a method of treating a subject having at least a partially occluded vessel comprising implanting a stent of the invention thereby to maintain patency of the vessel.

BRIEF DESCRIPTION OF THE DRAWINGS

The above and further advantages of the invention may be better understood by referring to the following description in conjunction with the accompanying drawings in which.

DETAILED DESCRIPTION

The stents of the invention are designed comprising at least one controlled fracture location and, in certain embodiments, controlled timing of the fracture. As such, the connection design and materials are suitable to provide the stent with, improved resistance to fatigue fractures at uncontrollable locations which can happen with stents presently in use. Fatigue fracture is a particular problem with stents deployed in tortuous vessels which stents are constantly subjected to torsion, twisting, bending and compression. Over time, the forces cause the stent to fatigue and break, sometime allowing jagged struts and end to pierce the adjacent vessel or hang into the lumen attracting thrombi. Such breakage can also compromise the support provided by the stent. Thus, the stents of the invention are designed to separate in such a manner so that when separation occurs the separation does not expose fragmented or jagged material and, importantly, the circumferential support provided by the stent does not become compromised. One method for accomplishing this is to provide for controlled separation or breakage at locations oriented at acute or greater angle relative to the circumference. The separation occurs at pre-determined locations via temporary joints. Several non-limiting examples are shown in the Figures to more clearly describe the features of the invention. Other designs of joints and connections can achieve the favorable outcomes of the invention.

Figure 1:
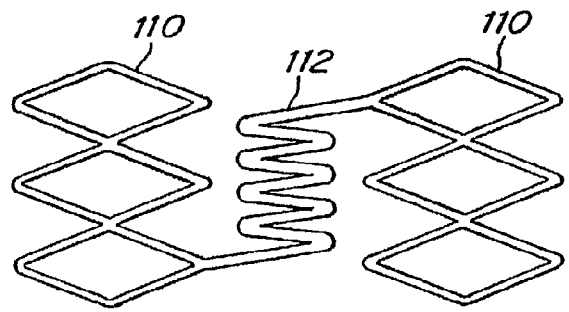
FIG. 1 is plan view of a flattened section of a stent comprising one embodiment of the invention.

FIG. 1 shows one embodiment of the invention. A flattened section of a stent is shown. The stent may be a hollow tube having a first end and a second end. The stent is comprised of two distinct patterns of alternating, circumferentially disposed segments. The terms "segment" and "section" are used herein to mean "one of several parts or pieces that fit with others to constitute a whole object". A first circumferential segment is comprised of a plurality of struts which are disposed along a first portion of the longitudinal axis of the stent and, which form a plurality of circumferentially disposed closed cells defined by the struts. The struts form diamond shaped cells 110 in the particular embodiment shown in FIG. 1. However, other suitable cell shapes, including both open and closed cells are also contemplated. In this embodiment, the diamond shaped cells are comprised of a plurality of peaks and valleys. The circumferentially disposed cells alternate along the longitudinal axis with a second circumferential segment comprising sinusoidal segments 112. The sinusoidal segments may be disposed in a partially circumferential manner. Disposed partially in a circumferential manner may mean, in some embodiments that the degree arc encompassed by the sinusoidal segment is less than 360°, less 270°, less than 180°, less than 90°, less than 60°, or less than 30°. Thus, because the sinusoidal segments are only partially disposed circumferentially, a plurality of sinusoidal segments is contemplated for each segment of the stent that alternates between the circumferentially disposed closed cells. The plurality of sinusoidal segments is thus sandwiched between circumferentially disposed closed cells. The circumferentially disposed closed cell segments thus lie adjacent to a plurality of sinusoidal segments traveling from one end of the stent, along the longitudinal axis to the other end. Both end positions along the longitudinal axis of the stent may be desirably occupied by circumferentially disposed cells. The sinusoidal segments are each joined to at least one circumferentially disposed cell of the first circumferential closed cell segment. In some embodiments the sinusoidal segment may be joined at a single position to one adjacent closed cell. In other embodiments the sinusoidal segment may be joined at more than one position to distinct adjacent cells, e.g., 2 distinct adjacent cells. The sinusoidal segments may desirably be joined at a peak position of one of the diamond shaped closed cells.

In certain embodiments the sinusoidal segments may expand independently of one another as the stent expands from its first diameter to its second diameter. Thus, the sinusoidal segments provide for a more flexible stent during deployment, while also providing for greater resistance to fatigue and fracture once the stent is deployed. The closed cells may be designed to provide for optimal radial strength.

Figure 2:
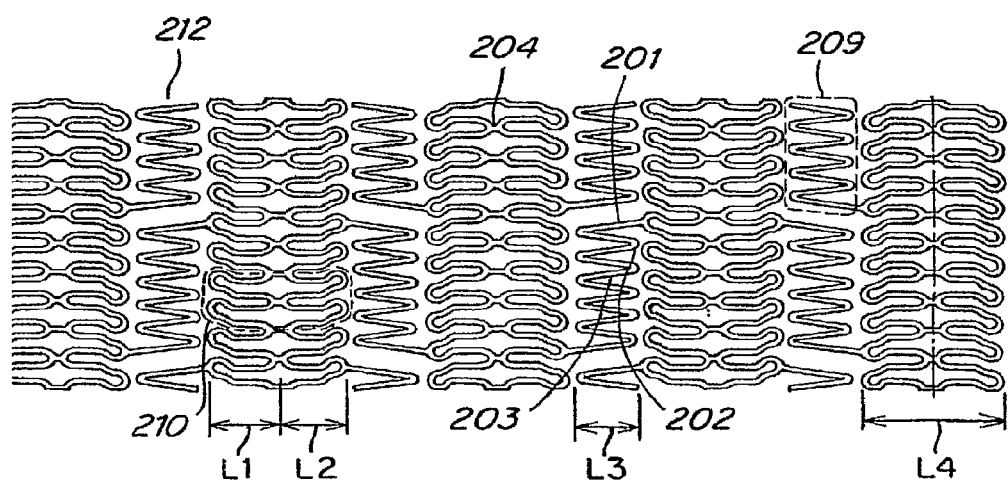
FIG. 2 is plan view of a flattened section of a stent comprising another embodiment of the invention.

An alternative embodiment of the invention is shown in FIG. 2. This embodiment is similar to the one described above for FIG. 1, except that a different closed cell structure is contemplated for the circumferentially disposed cells. In this embodiment a plurality of closed cells 210 are circumferentially disposed and are comprised of plurality of struts arranged in an undulating pattern forming a series of curved peaks and valleys. The closed cells are symmetrical about an axis orthogonal to the longitudinal axis of the stent. Individual cells are formed by joining points which exist at the valley formed between two adjacent cells. Valleys are located at positions closest to the circumferentially disposed axis which bisects the cell. Each cell is comprised of two peaks, each peak pointing towards an opposite end of the stent along the longitudinal axis of the stent. The open space comprising each of the peaks is narrower than the corresponding open center of the cell. The tips of the peaks are rounded and are radially disposed either inwardly, or outwardly, in an alternating pattern, in relation to the center of the hollow tube. Thus, cells radiating inwardly at the peak tips are separated from cells radiating outwardly at the peak tips by a plurality of sinusoidal segments 212 that are partially circumferentially disposed. A single connecting unit 209 which in this embodiment is sinusoidal is shown. A cell 210 in its pre-deployment position is also shown. For convenience, locations 201 through 204 are labeled to illustrate features of the invention when compared to presently available stents. Location 202 will enjoy similar radial strength, that is, the design will preserve the radial strength even after the controlled fracture. Certain embodiments will have locations 203 with a smaller profile which may be desirable in certain applications. Due to the design location 204 demonstrates improved flexibility.

Figure 3:
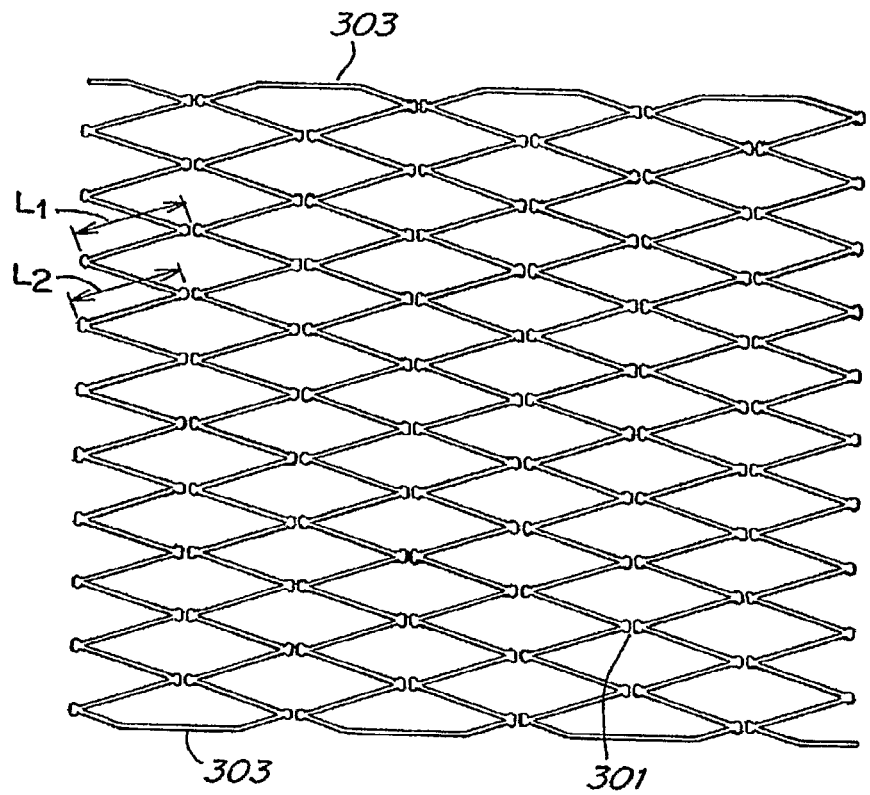
FIG. 3 is plan view of a flattened section of a stent comprising yet another embodiment of the invention.

FIG. 3 shows another embodiment of the invention. A flattened section of a stent is shown. The stent may be a hollow tube having a first and second end. The stent is comprised of a plurality of circumferentially disposed expandable segments. Each of these segments is comprised of a plurality of struts which may be circumferentially disposed in a zig-zag or Z pattern. The struts arranged in a zig-zag pattern form a plurality of peaks and valleys. Adjacent circumferentially disposed segments may be out of phase with each other (e.g. 180° out of phase). Thus, a valley on a first segment is proximal to a peak on an adjacent circumferentially disposed segment. Adjacent circumferentially disposed segments may be joined at a plurality of proximal peaks and valleys by temporary joints. In another embodiment, circumferentially disposed segments may be in phase. Thus, adjacent circumferentially disposed segments may be joined peak to peak. In this embodiment, a bridge 303 is marked which bridge connects the stent when it assumes its tubular form.

The temporary joint, however, may be strong enough to remain intact during deployment of the stent such that the stent has increased column strength and dimensional stability during loading of the stent on a catheter, as well as during the phases of delivery and deployment. The temporary joints may also be disposed to detach at different stress thresholds, such that adjacent circumferential segments remain interconnected at at least one or more selected locations designed to withstand the higher stress conditions. The temporary joints may also help prevent the stent from elongating or shrinking axially when it is radially expanded during deployment. In certain embodiments two adjacent circumferential segments will have a temporary joint wherever a peak or valley is proximal to a corresponding peak or valley on an adjacent circumferential segment. In other embodiments two adjacent circumferential segments may have about 1-8 temporary joints connecting them. In yet other embodiments two adjacent circumferential segments may not have any temporary joints connecting them. The temporary joints may be spatially offset from each other such as in a helically disposed manner, to facilitate increased flexibility, and to accommodate crimping of the stent without compromising the stent at the crimping location Referring to FIG. 3, the stent may thus be comprised of a first length ($L_1$) and a second length ($L_2$), where L1 represents the length of a perpendicular drawn from a first temporary joint to a first peak, the first peak being connected by a strut to the first temporary joint and $L_2$ represents the length between a second temporary joint adjacent to the first temporary joint and a second peak, the second peak being connected by a strut to the second temporary joint. The stent may also be comprised of a plurality of connecting bridges. The connecting bridges may be struts which additionally join adjacent circumferential segments. The connecting bridge thus joins a first strut from a first circumferential segment to a second strut from a second circumferential segment. The connecting bridge may be joined to the first and second struts at a position encompassing at least one temporary joint. The connecting bridge struts may be disposed parallel with the longitudinal axis of the stent. Other methods for increasing column strength include coating and/or covering the stent with polytetrafluoroethylene and/or expanded polytetrafluoroethylene or other biocompatible polymers (on one or both the inner and/or outer surface). Preferably, the coating/covering is bioabsorbable.

Figure 4:
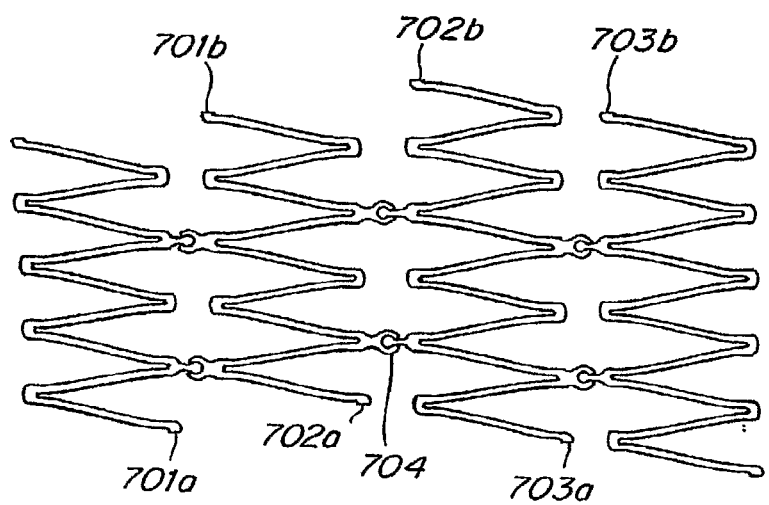
FIG. 4 is plan view of a flattened section of a stent comprising one embodiment of the invention.
Figure 5:
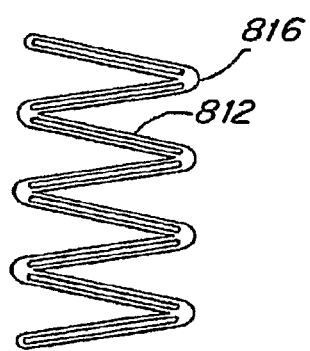
FIG. 5 is a plan view of a flattened section of a double strut stent segment.
Figure 6:
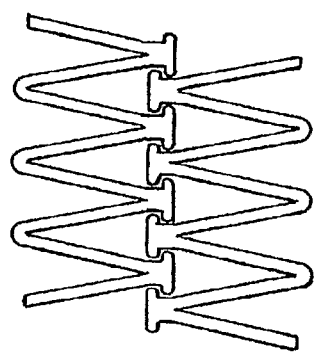
FIG. 6 shows another embodiment of a temporary joint.

FIG. 4 shows another embodiment of the invention. A flattened section of a stent is shown. The stent may comprise a hollow tube having a first and second end. The stent is comprised of a plurality of circumferentially disposed expandable segments. Each of these segments is comprised of a plurality of struts which may be circumferentially disposed in a zig-zag or Z pattern. The struts arranged in a zig-zag pattern form a plurality of peaks and valleys. Adjacent circumferentially disposed segments may be out of phase with each other. Thus a valley on a first segment is proximal to a peak on an adjacent circumferential segment. Adjacent segments may be joined at one point (e.g., locations 701, 702, 703) and thus the stent may be comprised of a plurality of contiguously attached struts that traverse the length of the stent from the first end to the second end in a staggered, alternating or spiral configuration. The circumferentially disposed segments may also be joined by a plurality of temporary joints. Temporary joints may be comprised of weak linkages that will break over time as a result of physiological stress after the stent is deployed. The temporary joints, however, may be strong enough to remain intact during deployment of the stent such that the stent has increased column strength during loading of the stent on a catheter, as well as delivery and deployment of the stent. Disengagement of these temporary joints facilitates deployment in a curved vessel or in a vessel which undergoes a change in diameter at me deployment site. The temporary joints may also help prevent the stent from longitudinally elongating or shrinking axially when it is radially expanded during deployment. In certain embodiments two adjacent circumferential segments will have a temporary joint wherever a peak or valley is proximal to a corresponding peak or valley on an adjacent circumferential segment. In other embodiments two adjacent circumferential segments may have about 1-8 temporary joints connecting them. The temporary joints may be comprised of a first interlocking structure and a second interlocking structure. The interlock structure may be comprised of an elongated member that is contiguous with a strut. FIG. 5 illustrates suitable location for a slotted connection. The first interlocking structure may comprise a male structure and the second interlocking structure may comprise a female structure adapted to receive the male structure. In FIG. 5 a slotted interlock structure (female) 812 is adapted to interlock with the male interlock structure (not shown) of an adjacent segment. 816 shows a non-slotted location where two struts meet. The male and female interlock structures may be round or oval in shape or may assume other geometrically interlocking structures, such as hooks illustrated in FIG. 6.

The temporary joints or connections described in the various embodiments may be comprised of relatively weak linkages (e.g., reduced width or thickness) or mechanical joints bound by mechanical means, such as adhesive glue, epoxy, and other polymers that will break over time as a result of physiological stress once the stent is deployed.

In the various embodiments of the invention, the temporary connections can be thermally bonded/welded, molded or otherwise physically attached the stent. In other embodiments, for example where the connections form a loop, they may not be physically attached to the stent except to the extent that they loop through the segment holes. In some embodiments, the temporary joints or connections may be attached to other polymeric coatings on the stent. For example, the stent may be coated with expanded polytetrafluoroethylene ("ePTFE") which can be bonded to the temporary joints and/or stent struts.

Any of the stents of the invention may be implemented with a double strut. Double strut stents have been previously described, see, e.g. U.S. Pat. Nos. 6,533,808, 6,132,461, 6,132,460 all of which are incorporated by reference in their entirety. Briefly, the double strut design provides for increased flexibility for ease of delivery and deployment, while maintaining optimal vessel support as well as radial (hoop) strength and column strength. The design provides for a plurality of slots in the struts comprising the stent. The slots are openings within the structure of the strut and may pass completely through the strut. In other embodiments, the slot is a groove or recess in the strut that does not extend completely through one dimension of the strut. Because the slots are contained within the strut they will have a length and a width that is less than the length and the width of the strut they are contained in.

Any method known in the art may be used to make the stents of the invention, e.g. chemical etching, electrochemical etching, electro-discharge machining (EDM), physical or chemical vapor disposition. The stent may be made from a hollow tube or from sheet materials. In certain embodiments the stent may be made by laser cutting the stent from a hollow tube. The hollow tube may be comprised of any biocompatible material. In one embodiment the hollow tube is comprised of shape memory polymer, shape memory alloy, or super elastic alloy, e.g. nitinol, or a Co—Cr alloy. Other suitable materials are well known in the art.

The skilled artisan will appreciate that the dimensions of the stent, as well as the dimensions of the struts comprising the stent may be varied to meet the needs of a particular application. For example in certain embodiments the number and length of the coiled segments may be varied depending on the flexibility desired for the particular application, as well as the length of the stent. The struts may be square or rectangular or circular in cross section. The strut thickness and width may vary along the length of the stent. In certain embodiments the strut thickness is in the range of about 0.002 inches to about 0.024 inches. In certain embodiments the struts may have a width in the range of about 0.002 inches to about 0.024 inches. The radial strength may vary along the length of the stent as well. In certain embodiments the radial strength may vary within the range of between about 5 and about-50 gram/mm.

The invention further provides a method of treating a subject having at least a partially occluded vessel comprising implanting a stent of the invention in the subject such that patency of the vessel is established or maintained. The vessel may include any vessel or duct within the subject, e.g. any portion of the circulatory system of the subject, including but not limited to the coronary arteries, carotid arteries and peripheral vasculature, as well as a biliary duct, a pancreatic duct and the like. The vessel may comprise a curved arterial lumen.

In certain embodiments the vessel stented may constitute a popiteal artery, a femoral artery, deep femoral artery, a brachial artery, a radial artery, an ulnar artery, a palmar arch, a posterior tibial artery, anterior tibial artery, external iliac artery, common iliac artery, internal iliac artery, descending genicular artery, and an axillary artery, as well as various venous vasculature.

The stent may be implanted in the subject using a minimally invasive procedure, e.g. by catheter and guide wire. The catheter may comprise a sheath and an elongated member. In certain embodiments the stent may be comprised of a shape memory material and thus be self expandable. In other embodiments a balloon catheter may be used to expand the stent upon deployment at the desired site.

Subject as used herein, refers to any animal. The animal may be a mammal. Examples of suitable mammals include, but are not limited to, humans, non-human primates, dogs cats, sheep, cows, pigs, horses, mice, rats, rabbits, and guinea pigs.

Treat, treatment, treating, as used herein means any of the following: the reduction in severity of a disease or condition; the reduction in the duration of a disease course; the amelioration of one or more symptoms associated with a disease or condition; the provision of beneficial effects to a subject with a disease or condition, without necessarily curing the disease or condition; the prophylaxis of one or more symptoms associated with a disease or condition.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

What is claimed is:

1. A stent comprising:
    a plurality of circumferentially disposed first segments, each first segment comprising a plurality of struts defining a plurality of closed cells having peaks; and
    a plurality of circumferentially disposed second segments, each second segment being sandwiched between two first segments, and each second segment comprising a plurality of sinusoidal struts, each sinusoidal strut being disposed in an arc about less than a circumference of the stent and connected to at least one first segment of the two first segments, wherein a second segment of the plurality of second segments comprises:
        a first sinusoidal strut having a first end and a second end; and
        a second sinusoidal strut having a third end and a fourth end, the second sinusoidal strut being circumferentially adjacent to the first sinusoidal strut,
    wherein, when a section of the stent including the first and second sinusoidal struts is flattened, the first and second ends of the first sinusoidal strut are offset from each other in a direction perpendicular to a longitudinal axis of the stent such that the first and second ends are aligned in a direction parallel to the longitudinal axis with different closed cells of the plurality of closed cells, and wherein when the section of the stent is flattened, the second end of the first sinusoidal strut and the third end of the second sinusoidal strut are both positioned between the first end of the first sinusoidal strut and the fourth end of the second sinusoidal strut in the direction perpendicular to the longitudinal axis, the second and third ends being offset from each other in the direction parallel to the longitudinal axis, and
    wherein when the section of the stent is flattened, the first and second ends of the first sinusoidal strut are spaced from each other in the direction perpendicular to the longitudinal axis by a distance greater than a length of one closed cell of the plurality of closed cells, the length being measured in the direction perpendicular to the longitudinal axis.

2. The stent of claim 1, wherein at least one sinusoidal strut of each second segment interconnects peaks of the closed cells of the two first segments between which the respective second segment is sandwiched.

3. The stent of claim 1, wherein each sinusoidal strut defines a plurality of peaks and valleys.

4. The stent of claim 1, wherein the sinusoidal struts of each second segment are configured to expand independently of one another.

5. The stent of claim 1, wherein the closed cells each have a diamond shape.

6. The stent of claim 1, wherein the plurality of struts of each first segment are arranged in an undulating pattern forming curved peaks and valleys.

7. The stent of claim 1, wherein each cell has two peaks, each peak pointing towards an opposite end of the stent along the longitudinal axis of the stent.

8. The stent of claim 7, wherein the tips of each of the two peaks are rounded.

9. The stent of claim 1, wherein the closed cells are each symmetrical about an axis orthogonal to the longitudinal axis of the stent.

10. The stent of claim 1, the first and second ends of the first sinusoidal strut being spaced from each other in the direction perpendicular to the longitudinal axis by a distance greater than a length of three closed cells of the plurality of closed cells, the length being measured in the direction perpendicular to the longitudinal axis.

11. The stent of claim 1, the first and second ends of the first sinusoidal strut being aligned in the direction parallel to the longitudinal axis with peaks of the different cells.

12. A stent comprising:
a plurality of circumferentially disposed first segments, each first segment comprising a plurality of struts defining a plurality of closed cells having peaks; and
a plurality of circumferentially disposed second segments, each second segment being sandwiched between two adjacent first segments, wherein each second segment comprises a plurality of sinusoidal struts, each sinusoidal strut defining a plurality of peaks and valleys and disposed in an arc about less than a circumference of the stent, wherein a second segment of the plurality of second segments comprises:
a first sinusoidal strut having a first end and a second end; and
a second sinusoidal strut having a third end and a fourth end,
wherein, when a section of the stent including the first and second sinusoidal struts is flattened, the first and second ends of the first sinusoidal strut are offset from each other in a direction perpendicular to a longitudinal axis of the stent such that the first and second ends are aligned in a direction parallel to the longitudinal axis with a different closed cells of the plurality of closed cells, and
wherein when the section of the stent is flattened, the first end of the first sinusoidal strut is joined at a first position to struts defining a first peak of a first closed cell of a first adjacent first segment, and the second end of the first sinusoidal strut is joined at a second position to struts defining a second peak of a second closed cell of a second adjacent first segment, and
wherein when the section of the stent is flattened the first and second ends of the first sinusoidal strut are spaced from each other in the direction perpendicular to the longitudinal axis by a distance greater than a length of one closed cell of the plurality of closed cells, the length being measured in the direction perpendicular to the longitudinal axis.

13. The stent of claim 12, wherein the sinusoidal struts of each second segment are configured to expand independently of one another.

14. The stent of claim 12, wherein the closed cells each have a diamond shape.

15. The stent of claim 12, wherein the plurality of struts of each first segment are arranged in an undulating pattern forming curved peaks and valleys.

16. The stent of claim 12, wherein each cell has two peaks, each peak pointing towards an opposite end of the stent along the longitudinal axis of the stent.

17. The stent of claim 16, wherein the tips of each of the two peaks are rounded.

18. The stent of claim 12, wherein the closed cells are each symmetrical about an axis orthogonal to the longitudinal axis of the stent.

19. The stent of claim 12, the first and second ends of the first sinusoidal strut being spaced from each other in the direction perpendicular to the longitudinal axis by a distance greater than a length of three closed cells of the plurality of closed cells, the length being measured in the direction perpendicular to the longitudinal axis.

20. A method comprising:
introducing a stent into a vessel of a patient, the stent comprising:
a plurality of circumferentially disposed first segments, each first segment comprising a plurality of struts defining a plurality of closed cells having peaks; and
a plurality of circumferentially disposed second segments, each second segment being sandwiched between two first segments, and each second segment comprising a plurality of sinusoidal struts, each sinusoidal strut being disposed in an arc about less than a circumference of the stent and connected to at least one first segment of the two first segments, wherein a second segment of the plurality of second segments comprises:
a first sinusoidal strut having a first end and a second end; and
a second sinusoidal strut having a third end and a fourth end, the second sinusoidal strut being circumferentially adjacent to the first sinusoidal strut,
wherein, when a section of the stent including the first and second sinusoidal struts is flattened, the first and second ends of the first sinusoidal strut are offset from each other in a direction perpendicular to a longitudinal axis of the stent such that the first and second ends are aligned in a direction parallel to the longitudinal axis with different closed cells of the plurality of closed cells, and wherein when the section of the stent is flattened, the second end of the first sinusoidal strut and the third end of the second sinusoidal strut are both positioned between the first end of the first sinusoidal strut and the fourth end of the second sinusoidal strut in the direction perpendicular to the longitudinal axis, the second and third ends being offset from each other in the direction parallel to the longitudinal axis, and
wherein when the section of the stent is flattened, the first and second ends of the first sinusoidal strut are spaced from each other in the direction perpendicular to the longitudinal axis by a distance greater than a length of one closed cell of the plurality of closed cells, the length being measured in the direction perpendicular to the longitudinal axis; and
expanding the stent within the vessel of the patient.

21. The method of claim 20, wherein expanding the stent comprises expanding the stent via a balloon catheter.

22. The method of claim 20, wherein the stent is self-expandable, and wherein expanding the stent comprises releasing the stent from a sheath.

23. The method of claim 20, wherein each sinusoidal strut defines a plurality of peaks and valleys.

* * * * *